United States Patent
Shana'a

[11] Patent Number: 5,851,978
[45] Date of Patent: Dec. 22, 1998

[54] SOAP COMPOSITION

[75] Inventor: May Shana'a, Fort Lee, N.J.

[73] Assignee: Lever Brothers Company, Division of Conopco, Inc., New York, N.Y.

[21] Appl. No.: 728,583

[22] Filed: Oct. 10, 1996

Related U.S. Application Data

[63] Continuation of Ser. No. 469,949, Jun. 6, 1995, abandoned.

[30] Foreign Application Priority Data

Jul. 19, 1994 [GB] United Kingdom ............... 9414572

[51] Int. Cl.$^6$ ................ C11D 3/02; C11D 3/16
[52] U.S. Cl. .......... 510/417; 510/121; 510/126; 510/129; 510/130; 510/131; 510/136; 510/159
[58] Field of Search .................. 510/121, 122, 510/129, 135, 136, 159, 417, 130

[56] References Cited

U.S. PATENT DOCUMENTS

| | | | |
|---|---|---|---|
| 4,772,471 | 9/1988 | Vanlerberghe et al. | 424/450 |
| 5,021,200 | 6/1991 | Vanlerberghe et al. | 264/4.3 |
| 5,198,470 | 3/1993 | Zysonan et al. | 514/785 |
| 5,393,450 | 2/1995 | Shana'a | 252/170 |
| 5,411,742 | 5/1995 | Sebag et al. | 424/450 |
| 5,439,672 | 8/1995 | Zabotto et al. | 424/59 |
| 5,612,307 | 3/1997 | Chambers et al. | 510/406 |

FOREIGN PATENT DOCUMENTS

| | | |
|---|---|---|
| 94/01084 | 1/1994 | WIPO . |
| 94/01085 | 1/1994 | WIPO . |

*Primary Examiner*—Kery Fries
*Attorney, Agent, or Firm*—Ronald A. Koatz

[57] ABSTRACT

An aqueous cleansing and moisturising composition comprising 5–35 wt. % $C_8$ to $C_{22}$ fatty acid; up to 10 wt. % of a surface active agent, a benefit agent having a weight average particle size in the range 15 to 500 microns and structurant. The structurant is a material which causes the composition to adopt the lamellar phase or a material which structures the continuous liquid phase or a mixture thereof. The composition is substantially free of insoluble solid fatty acid or fatty acid soap.

3 Claims, No Drawings

SOAP COMPOSITION

This is a Continuation application of Ser. No. 08/469,949, filed Jun. 6, 1995 now abandoned.

The present invention relates to soap compositions suitable for the care and personal washing of the skin. In particular, it relates to compositions which are formulated to give mild cleansing and conditioning of the skin.

Compositions formulated to cleanse the skin are well known. It is also known to formulate products which provide both a cleansing and a moisturising benefit.

For example WO 94/01084 discloses a soap based composition comprising potassium $C_8$–$C_{22}$ fatty acid soap, water, a polyol, petrolatum and $C_8$–$C_{22}$ free fatty acid. According to this reference the use of petrolatum particles with a particle size in the range 45 to 120 microns results in improved deposition of petrolatum onto the skin. The composition is stable by virtue of the insoluble fatty acid soap which acts as the structurant, with the polyol which forms part of the aqueous phase existing between individual crystals of the fatty acid soap.

A similar system is described in WO 94/01085 which discloses semi-solid soap compositions comprising potassium $C_8$–$C_{22}$ fatty acid soap, water, a polyol, petrolatum and $C_8$–$C_{22}$ free fatty acid.

A disadvantage with such system is that they contain high levels of insoluble free fatty acid and soap. This high level of solid phase in the compositions may adversely affect the amount of emollient oil for example petrolatum, deposited onto the skin when the composition is used.

We have now found that aqueous soap based compositions comprising large particles, by "particles" is meant a solid particle or liquid droplet, of benefit agent can be formulated with alternative structuring systems.

Thus, according to the invention there is provided an aqueous liquid cleansing and moisturising composition comprising:

a) from 5 to 35% by weight of a $C_8$ to $C_{22}$ fatty acid;
b) from 0 to 10% by weight of a surface active agent;
c) a benefit agent having a weight average particle size in the range 15 to 500 microns; and
d) a structurant selected from materials which cause the composition to adopt the lamellar phase; materials which structure the continuous liquid, phase and mixtures thereof;

and the composition being substantially free of insoluble solid fatty acid or fatty acid soap.

By "substantially free" of insoluble solid fatty acid or fatty acid soap is meant the level of solid fatty acid or solid fatty acid soap is such that it does not interfere with the deposition of the benefit agent and, preferably, that it is below 2% by weight.

Using a structurant as defined above it is possible to suspend particles of benefit agent having a weight average particle size in the range 15 to 500 microns, preferably 20 to 200 microns.

An advantage of the composition according to the invention is that during use it deposits benefit agent onto the skin at a level which results in a perceivable benefit. Without being bound by theory, it is believed the benefit agent is dispersed into large pools during dilution of the composition in use and these pools deposit readily onto the skin.

The composition is suitable for cleansing and "moisturising" "conditioning", or "protection" of the skin. The benefit agent is included in the composition to moisturise, condition and/or protect the skin. By "emollient" oil is meant a substance that softens the skin (stratum corneum) and keeps it soft by retarding the decrease of its water content and/or protects the skin.

Preferred benefit agents include a) silicone oils, gums and modifications thereof such as linear and cyclic polydimethylsiloxanes; amino, alkyl alkylaryl and aryl silicone oils;

b) fats and oils including natural fats and oils such as jojoba, soyabean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;

c) waxes such as carnauba, spermaceti, beeswax, lanolin and derivatives thereof;

d) hydrophobic plant extracts;

e) hydrocarbons such as liquid paraffins, petrolatum, microcrystalline wax, ceresin, squalene, squalane, and mineral oil;

f) higher alcohols such as lauryl, cetyl, steryl, oleyl, behenyl, cholesterol and 2-hexadecanol alcohol;

g) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;

h) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;

i) lipids such as cholesterol, ceramides, sucrose esters and pseudo-ceramides as described in European Patent Specification No. 556 957;

j) vitamins such as vitamin A and E, and vitamin alkyl esters, including those vitamin C alkyl esters;

k) sunscreens such as octyl methoxyl cinnamate (Parsol MCX) and butyl methoxy benzoylmethane (Parsol 1789)

l) Phospholipids; and m) mixtures of any of the foregoing components.

The benefit agent may be incorporated in a carrier in the compositions of the invention, particularly if it is likely to suffer detrimental interactions with other components of the composition. Benefit agents for which such detrimental inter-actions may occur include lipids; alkyl lactates; sunscreens; esters such as isopropyl palmitate and isopropyl myristate; and vitamins. The carrier can, for example, be a silicone or hydrocarbon oil which is not solubilised/micellised by the surface active phase and in which the benefit agent is relatively soluble.

Particularly preferred benefit agents include silicone oils, gums and modifications thereof; esters such as isopropyl palmitate and myristate; and alkyl lactates.

The benefit agent is preferably present in amount of from 0.1 to 15 wt. %, most preferably from 0.2 to 10 wt. %, more preferably from 0.5 to 7 wt. %.

The structurant is selected from materials which cause the composition to adopt the lamellar phase and, in particular, the fatty acid present in the composition, $C_8$ to $C_{22}$ fatty alcohols, and ethoxylated alcohols; and materials which structure the continuous phase, i.e. the aqueous phase of the composition, such as swelling clays, for example laponite, and cross-linked polyacrylates such as Carbopol (TM) (polymers available from Goodrich); and mixtures of structurants. If a fatty acid is used as the structurant then it should preferably be selected from caproic, lauric, myristic and oleic fatty acid and 20 to 50 weight % of fatty acid in the composition should be free fatty acid, i.e. in the unneutralised form in the lamellar phase.

Of the clays particularly preferred are synthetic hectorite (laponite) clay used inconjunction with an electrolyte salt capable of causing the clay to swell thicken so as to suspend the benefit agent. Suitable electrolytes include alkali and alkaline earth salts such as halides, ammonium salts and sulphates.

Particularly preferred structurants are fatty acid, clay or a mixture thereof.

The fatty acids particularly preferred for the present invention are caproic, lauric, myristic and oleic fatty acids and mixtures thereof. It is particularly preferred to use a combination of oleic and lauric acids or a combination of oleic, lauric and myristic acids. Preferably the total level of fatty acid is from 10 to 35% by weight of the composition. Preferably at least 30% of the total fatty acid is in the free fatty acid form.

The compositions of the present invention will preferably contain from 1 to 8% wt. of a surface active agent. The surface active agent can be selected from any known surfactant suitable for topical application to the human body. Mild surfactants, i.e. surfactants which do not damage the stratum corneum, the outer layer of the skin, are particularly preferred.

One preferred anionic detergent is fatty acyl isethionate of formula:

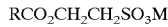
$$RCO_2CH_2CH_2SO_3M$$

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or coconut/palm blends.

Another preferred anionic detergent is alkyl ether sulphate of formula:

$$RO(CH_2CH_2O)_nSO_3M$$

where R is an alkyl group of 8 to 22 carbon atoms, n ranges from 0.5 to 10, especially 1.5 to 8, and M is a solubilising cation as defined above.

Other possible anionic detergents include alkyl glyceryl ether sulphate, sulphosuccinates, taurates, sarcosinates, sulphoacetates, alkyl phosphate, alkyl phosphate esters and acyl lactates, alkyl glutamates and mixtures thereof.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein $R^5$ ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially $C_8$–$C_{20}$ aliphatic alcohols ethoxylated with an average of from 1 to 20 moles of ethylene oxide per mole of alcohol.

It is also preferable that the composition includes from 0.5 to 10 wt. % of a cosurfactant with skin-mildness benefits. Suitable materials are zwitterionic detergents which have an alkyl or alkenyl group of 7 to 18 carbon atoms and comply with an overall structural formula:

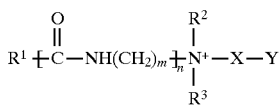

where $R^1$ is alkyl or alkenyl of 7 to 18 carbon atoms $R^2$ and $R^3$ are each independently alkyl, hydroxyalkyl or carboxyalkyl of 1 to 3 carbon atoms;

m is 2 to 4;

n is 0 or 1;

X is an alkylene of 1 to 3 carbon atoms, optionally substituted with hydroxyl; and Y is $-CO_2^-$ or $-SO_3^-$ Zwitterionic detergents within the above general formula include simple betaines of formula:

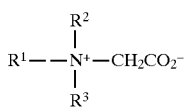

and amido betaines of formula:

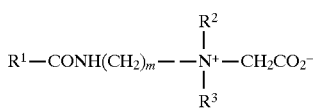

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the group $R^1$ has 10 to 14 carbon atoms. $R^2$ and $R^3$ are preferably methyl.

A further possibility is a sulphobetaine of formula:

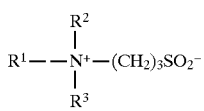

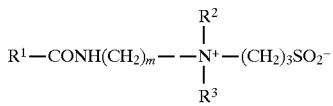

where m is 2 or 3, or variants of these in which $-(CH_2)_3 SO_3^-$ is replaced by

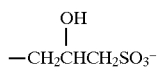

$R^1$, $R^2$ and $R^3$ in these formulae are as defined previously.

The compositions according to the invention may also comprise a thickening agent, i.e. a material which maintains the viscosity of the composition as the shear rate thereof is increased during use. Suitable materials include cross-linked polyacrylates such as Carbopol (TM) (polymers available from Goodrich); natural gums including alginates, guar, xanthan and polysaccharide derivatives including carboxy methyl cellulose and hydroxypropyl guar; propylene glycols and propylene glycol oleates; salts such as sodium chloride, ammonium sulphate; glycerol tallowates; and mixtures thereof.

Further examples of thickeners are given in the International Cosmetic Ingredient Dictionary, Fifth Edition, 1993, published by CFTA (the Cosmetic, Toiletry & Fragrance Association), incorporated herein by reference.

Furthermore, the benefit agent may also function as a carrier to deliver efficacy agents to skin treated with the compositions of the invention. This route is particularly useful for delivering efficacy agents which are difficult to deposit onto the skin or those which suffer detrimental interactions with other components in the composition. In such cases the carrier is a often a silicone or hydrocarbon oil which is not solubilised/micellised by the surface active phase and in which the efficacy agent is relatively soluble. Examples of such efficacy agents include anti-viral agents; hydroxycaprylic acids; pyrrolidone; carboxylic acids; 2,4, 4'-trichloro-2'-hydroxydiphenyl ether (Irgasan DP300); 3,4, 4'-trichlorocarbanilide; salicylic acid; benzoyl peroxide; perfumes; essential oils; germicides and insect repellants such as N,N-dimethyl m-toluamide (DEET); and mixtures thereof.

Compositions of the invention may be formulated as products for washing the skin, for example bath or shower gels, hand washing compositions, facial washing liquids; pre- and post-shaving products; rinse-off and wipe-off skin care products.

The compositions of the invention will generally be pourable liquids or semi-liquids for example pastes and will have a viscosity in the range 250 to 100,000 mPas measured at a shear rate of $10s^{-1}$ and 25° C. in a Haake Rotoviscometer RV20.

When the product is formulated as a shower gel the viscosity will generally be in the range 800 to 8000 mPas measured at a shear rate of $10s^{-1}$ at 25° C., with the lower viscosity products finding particular application in the Japanese market.

When the product is formulated as a facial wash product the viscosity will generally be in the range 5000 to 100,000 mPas measured at a shear rate of $10s^{-1}$ at 25° C.

In general, the compositions will exhibit an extrapolated Newtonian viscosity at a shear stress of 0.01 at 25° C. of at least 5,000 Pas, preferably greater than 10,000 Pas.

The above-mentioned characteristic viscosity measurements may be determined exactly (as in the case of the non-zero shear viscosities) using, for example a Carrimed CSL low shear rheometer, or obtained from an extrapolation according to the Cross Model (see J of the Chemical Engineer, 1993, paper entitled "Rheology for the Chemical Engineer" by H Barnes) as in the case of the zero shear rate.

Other typical components of the such compositions include opacifiers, preferably 0.2 to 2.0 wt. %; preservatives, preferably 0.2 to 2.0 wt. % and perfumes, preferably 0.5 to 2.0 wt. %.

The invention will be further illustrated by reference to the following non-limiting examples.

EXAMPLES

In the examples: Behenyl alcohol was Nacol 22-97 ex Condea. Coco amidopropyl betaine Rewoteric AMB14kS ex Rewo. Glycerol was from Unichema. Silicone oil was DC200, a polydimethylsiloxane ex Dow Corning.

The compositions were prepared as follows:

1. The water phase was prepared in the main vessel of a Becomix RW 30 mixer by adding water, electrolyte, soluble coactives such as betaine and any other soluble minor additives. The mixture was heated to 75° C.
2. When clay is used as a structurant it should be fully hydrated in cold water in the main vessel of the mixer before the addition of any of the ingredients in step 1.
3. The fatty acids are added to the water phase one at a time starting with Oleic, Lauric, Myristic and finally any others, while maintaining the temperature at 75° C. The fatty acids must be molten before any vacuum is applied.
4. Potassium hydroxide solution (40%) was added via a homogeniser. The system was stirred to dissolve any fatty acid soap while maintaining the temperature at 75° C. and a vacuum.
5. If ethylene glycol distearate (EGDS) is present it is added at step 4.
6. Thereafter silicone oil is added. The resultant mixture is then cooled to 40° C.
7. The mixture is then sampled for particle size distribution. The mixing time, speed and the product viscosity affect the particle size distribution. These can be adjusted to ensure particles of the required size are obtained.
8. Perfume and preservative are then added.
9. Thereafter the vacuum is released and the product discharged.

A number of tests were carried out by human volunteers. The experimental procedure employed was as follows:

The volunteer washed one forearm with a control shower gel of composition I but from which the silicone oil is absent. The procedure involved wetting the arm and also the volunteer's free hand with warm water then using the free hand to lather the arm with 0.5 grams of the control shower gel, next rinsing for 10 seconds while rubbing with the free hand and then drying the arm with a paper towel.

The volunteer then washed the other forearm with a test product using the same procedure. When drying the forearm care is taken that the paper towel is drawn only once across a test area of the forearm.

10 minutes after drying the forearm the volunteer pressed a strip of adhesive tape onto the areas on both forearms keeping it in place for 30 seconds using a spring loaded device bearing on a rubber bung to press the tape onto the skin with a repeatable pressure of 85 g.cm$^{-2}$. The adhesive tape employed was J-Lar Superclear (TM) tape having a width of 25 mm. Two strips of tape were applied to each forearm in this way to consecutive areas of the skin.

In this test procedure silicone which has deposited on the skin will subsequently be transferred to the tape along with some of the outer layer of the volunteer's skin.

The amounts of silicon and skin adhering to the tape are determined by means of X-ray fluorescence spectroscopy. The tape strips are placed in an X-ray fluorescence spectrometer with the adhesive side facing the beam of this machine. A mask is applied over the tape to define a standardised area in the middle of the tape which is exposed to the X-ray beam. The sample chamber of the machine is placed under vacuum before making measurements and the spectrometer is then used to measure the quantities of silicon and sulphur. The sulphur is representative of the amount of skin which has transferred to the tape.

This gave two sets of results:

A—control

B—composition according to the invention.

The average results for A were subtracted from the average results for B and the final value expressed as a ratio of silicon to sulphur.

Example I

In this example the variation in deposition of silicon with the particle size of silicone oil incorporated in a composition was examined.

| Composition I | % wt |
| --- | --- |
| Oleic Acid | 6.8 |
| Lauric Acid | 6.8 |
| Myristic Acid | 6.4 |
| Cocoamidopropyl betaine | 5 |
| Silicone oil | 5 |
| Sodium Chloride | 0.5 |
| Perfume | 1.0 |
| Potassium Hydroxide | 4.0 |
| Preservative and water to | 100 |
| Viscosity (shear rate of 10 s$^{-1}$ at 25° C.) | 1000 mPas |
| Results | |
| Droplet size of silicone oil | Si:S |
| 0.2 micron | 0.5 (Comparative example) |
| 20 micron | 2.0 |
| 40 micron | 2.9 |

The results show improved deposition as the droplet size of the silicone oil benefit agent increases.

Example II

This example demonstrates the effect of insoluble fatty acid soap on deposition of silicon. (Composition C is a comparative example).

| | % wt | |
| --- | --- | --- |
| Composition | II | C |
| Myristic Acid | 12 | 12 |
| Stearic/Palmitic Acid | 6.9 | 6.9 |
| Cocoamidoproyl betaine | 5.0 | 5.0 |
| Behenyl alcohol | 0.0 | 5.0 |
| Silicone oil | 5.0 | 5.0 |
| Clay | 2.0 | 0.0 |
| Sodium chloride | 1.0 | 0.5 |
| Potassium hydroxide* | to 100 | |
| Water & minors | | |

*as required to give pH no less than 9.2

Samples of the two compositions were examined under a microscope to establish whether crystals were present.

| Sample | particle size of benefit agent | Si:S |
| --- | --- | --- |
| II (substantially no crystals present) | 0.2 micron | 0.8 |
| C (crystals present) | 0.2 micron | 0.7 |
| II | 60 micron | 3.9 |
| C | 60 micron | 1.0 |

The results show there is no effective difference in deposition when the particle size of the silicone oil is small.

However, they show the benefit of reducing the amount of insoluble fatty acid soap when the composition contains larger particle size silicone oil.

Example III

In this example deposition of silicon from three compositions structured in different ways was compared.

IIIa is a lamellar structured composition. IIIb is a clay structured composition. D (comparison) is a composition structured with a high solid phase (insoluble free fatty acid and soap).

| | % wt |
| --- | --- |
| Composition IIIa | |
| Oleic Acid | 6.8 |
| Lauric Acid | 6.8 |
| Myristic Acid | 6.4 |
| Cocoamidopropyl betaine | 5.0 |
| Silicone oil | 5.0 |
| Potassium hydroxide | 3.5 |
| EGDS | 1.5 |
| Preservative | 0.05 |
| Ethylene diamine teraacetic acid (EDTA) | 0.02 |
| Sodium Chloride | 0.5 |
| Water + minors | to 100 |
| Composition IIIb | |
| Oleic Acid | 6.8 |
| Myristic Acid | 4.4 |
| Lauric Acid | 5.8 |
| Cocoamidoproyl betaine | 5.0 |
| Silicone oil | 5.0 |
| Laponite | 1.5 |
| Sodium chloride | 0.5 |
| Potassium hydroxide | 4.0 |
| Water & minors | to 100 |
| Composition D | |
| Stearic Acid | 7.9 |
| Paimitic Acid | 6.8 |
| Myristic Acid | 9.5 |
| Lauric Acid | 3.5 |
| Glycerol | 14.8 |
| Silicone oil | 5.0 |
| Potassium hydroxide | 3.8 |
| Water + minors | to 100 |

Samples of the three compositions were examined under a microscope to establish whether crystals were present. Crystals were only observed in composition D.

The compositions were tested by the procedure described above and the following results, an average of 10 experiments, obtained. Four separate tests were carried out.

| Test | Composition | Si:S IIIa | IIIb | D |
|------|-------------|-----------|------|------|
| 1 | | 4.43 | — | 2.03 |
| 2 | | — | 3.67 | 2.60 |
| 3 | | 4.0 | 3.23 | |
| 4 | | 3.73 | — | 2.5 |

The results demonstrate the advantage of the structuring systems according to the invention over a composition structured with a high solid phase.

I claim:

1. An aqueous liquid cleansing and moisturizing composition comprising the following:
   (A) from 5% to 35% by weight of fatty acids wherein said fatty acids comprise at least three fatty acids selected from the consisting of oleic acid, lauric acid, myristic acid, stearic acid, palmitic acid, and caproic acid;
   (B) from 1% to 8% of a surface active agent;
   (C) from 1% to 15% of silicone oil having an average particle size in the range of 15 to 500 microns which acts as a benefit agent; and
   (D) clay which acts as a structurant wherein said aqueous liquid cleansing and moisturizing composition being substantially free of insoluble solid fatty acid and fatty acid soaps.

2. An aqueous liquid cleansing and moisturizing composition according to claim 1 further comprising additional adjuvants selected from the group consisting of opacifiers, preservatives, perfumes, and mixtures thereof.

3. A method of depositing a benefit agent from an aqueous cleansing and moisturizing composition, the method comprising contacting with the skin with a silicone oil benefit agent in a composition comprising:
   (A) from 5% to 35% by weight of fatty acids wherein said fatty acids comprise at least three fatty acids selected from the group consisting of oleic acid, lauric acid, myristic acid, stearic acid, palmitic acid, and caproic acid;
   (B) from 1% to 8% of a surface active agent;
   (C) from 1% to 15% of silicone oil having an average particle size in the range of 15 to 500 microns which acts as a benefit agent; and
   (D) clay which acts as a structurant wherein said aqueous liquid cleansing and moisturizing composition being substantially free of insoluble solid fatty acid and fatty acid soaps.

* * * * *